(12) United States Patent
Dehdashtian et al.

(10) Patent No.: US 12,329,640 B2
(45) Date of Patent: Jun. 17, 2025

(54) SYSTEM AND METHOD FOR TRANSAORTIC DELIVERY OF A PROSTHETIC HEART VALVE

(71) Applicant: EDWARDS LIFESCIENCES CORPORATION, Irvine, CA (US)

(72) Inventors: Mark M. Dehdashtian, Irvine, CA (US); Teodoro S. Jimenez, Aliso Viejo, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

(21) Appl. No.: 18/544,266

(22) Filed: Dec. 18, 2023

(65) Prior Publication Data

US 2024/0115380 A1 Apr. 11, 2024

Related U.S. Application Data

(60) Continuation of application No. 16/178,537, filed on Nov. 1, 2018, now Pat. No. 11,896,485, which is a division of application No. 14/215,399, filed on Mar. 17, 2014, now Pat. No. 10,149,757.

(60) Provisional application No. 61/794,889, filed on Mar. 15, 2013.

(51) Int. Cl.
*A61F 2/24* (2006.01)

(52) U.S. Cl.
CPC .......... *A61F 2/2433* (2013.01); *A61F 2/2412* (2013.01); *A61F 2/2418* (2013.01)

(58) Field of Classification Search
CPC ..... A61F 2/2433; A61F 2/2412; A61F 2/2418
See application file for complete search history.

(56) References Cited

U.S. PATENT DOCUMENTS

| 6,264,683 B1 * | 7/2001 | Stack | A61F 2/958 623/1.11 |
|---|---|---|---|
| 2002/0138128 A1 * | 9/2002 | Stiger | A61F 2/958 623/1.11 |
| 2007/0112422 A1 * | 5/2007 | Dehdashtian | A61F 2/2427 623/2.11 |
| 2007/0282367 A1 * | 12/2007 | Jeffrey | A61F 2/958 606/194 |

* cited by examiner

*Primary Examiner* — Jing Rui Ou
(74) *Attorney, Agent, or Firm* — Scott R. Hansen; Joel B. German (57) ABSTRACT

A delivery system and method for delivering a prosthetic heart valve to the aortic valve annulus via a transaortic approach. The system includes a balloon catheter for delivering a balloon-expandable prosthetic heart valve through an introducer from an approach from outside the patient, through a minimally-invasive opening in the chest cavity through an incision in the aorta, and into the aorta and aortic annulus. The balloon catheter includes a flexible, tapered tip just distal of the balloon to facilitate positioning of the prosthetic heart valve in the proper orientation within the aortic annulus. The prosthetic heart valve may be installed over the existing calcified leaflets, and a pre-dilation valvuloplasty procedure may also be utilized.

15 Claims, 11 Drawing Sheets

SYSTEM AND METHOD FOR TRANSAORTIC DELIVERY OF A PROSTHETIC HEART VALVE

CROSS-REFERENCE TO RELATED APPLICATIONS

This application is a continuation of U.S. patent application Ser. No. 16/178,537, filed Nov. 1, 2018, which is a divisional of U.S. patent application Ser. No. 14/215,399, now U.S. Pat. No. 10,149,757, filed Mar. 17, 2014, which claims priority to U.S. Provisional Patent Application No. 61/794,889, filed Mar. 15, 2013, all of which are incorporated by reference herein in their entireties.

FIELD OF THE INVENTION

The present invention relates to methods and systems used to deliver a prosthetic valve to a heart. More specifically, the present invention relates to methods and apparatus for transaortically replacing a heart valve without opening the chest cavity and with or without placing the patient on bypass, the latter being termed "off-pump."

BACKGROUND OF THE INVENTION

Heart valve replacement may be indicated when there is a narrowing of the native heart valve, commonly referred to as stenosis, or when the native valve leaks or regurgitates, such as when the leaflets are calcified. When replacing the valve, the native valve may be excised and replaced with either a biologic or a mechanical valve.

Conventional heart valve surgery is an open-heart procedure conducted under general anesthesia. An incision is made through the patient's sternum (sternotomy), and the patient's heart is stopped while blood flow is rerouted through a heart-lung "cardiopulmonary" bypass machine. In recent years, advancements in "minimally-invasive" surgery and interventional cardiology have encouraged some investigators to pursue percutaneous replacement of the aortic heart valve. Minimally invasive heart valves are known using expandable stents as anchors for a valve structure. Edwards Lifesciences has developed a balloon-expandable stent integrated with a bioprosthetic valve, which is known as the SAPIEN® valve. The stent/valve device is deployed across the native diseased valve to permanently hold the valve open, thereby alleviating a need to excise the native valve. The SAPIEN® device may be delivered in a cardiac catheterization laboratory under local anesthesia using fluoroscopic guidance, thereby avoiding general anesthesia and open-heart surgery.

U.S. Patent Publication No. 2002/0151970 to Garrison et al. describes a two-piece device for replacement of the aortic valve that is adapted for delivery through a patient's aorta. A stent is endovascularly placed across the native valve, then a replacement valve is positioned within the lumen of the stent and connected thereto. By separating the stent and the valve during delivery, a so-called "two-stage" approach, the profile of the delivery system can be reduced. Both the stent and a frame of the replacement valve may be balloon- or self-expandable.

Some researchers propose implanting prosthetic heart valves at the aortic annulus through a ventricular approach. For instance, Christoph H. Huber of the Brigham and Women's Hospital of Harvard Medical School, and others, have proposed a procedure in which a self-expanding valve stent is implanted at the aortic position using a direct-access transapical approach. (E.g., Huber, et al. Direct-access valve replacement a novel approach for off-pump valve implantation using valved stents. J Am Coll Cardiol 2005; 46:366-70). More recently, Bergheim in U.S. Patent Publication No. 2005/0240200 discloses another transapical approach in which either a balloon- or self-expanding valve may be implanted, and also proposes removing or decalcifying stenotic valves. U.S. patent application Ser. No. 11/280,063, filed Nov. 16, 2005, the entire contents of which are expressly incorporated herein by reference, discloses a transapical heart valve delivery system and method, where an expandable prosthetic heart valve is delivered to a desired position via an incision in the apex of the heart.

The selection of the best method for replacing a heart valve is highly dependent upon the condition of a particular patient. For some patients, traditional open heart surgery can be the preferred option. For other patients, such as those who are in extremely frail condition, a minimally-invasive implantation may be desired. It is important for the treating physician to have multiple options for prosthetic heart valve replacement, in order to best serve the needs of a particular patient.

There is a need for additional and improved methods and apparatuses for replacing a heart valve without open-heart surgery or cardiopulmonary bypass. The current invention satisfies this need.

SUMMARY OF THE INVENTION

Preferred embodiments of the present invention provide a heart valve delivery system for delivery of a prosthetic (i.e., replacement) heart valve to a native valve site without an open chest procedure. Methods according to the invention may include a transaortic approach, wherein an incision is made in the aorta through which a valve delivery catheter is advanced. The delivery system includes a valve delivery catheter having a distal tapered tip, which may have a curved portion, to facilitate advancement and positioning of the valve in a native valve, such as a calcified aortic valve.

In accordance with one aspect, the present invention provides an off-pump, minimally-invasive surgical method of implanting a prosthetic heart valve to an aortic valve annulus of a patient, which may be performed while the patient's heart remains beating. The method includes providing a balloon-expandable prosthetic heart valve mounted over a balloon on a distal end of a balloon catheter. The physician creates a small puncture in the chest wall, and then creates a puncture through the wall of the aorta at or near the aortic arch. The physician then advances an introducer sheath through the respective punctures (i.e., through the chest wall and the aortic wall) and into a position above the aortic valve. A delivery catheter, with the prosthetic valve on its distal end, is passed through the introducer sheath into the ascending aorta. The distal end of the delivery catheter is advanced to cross the aortic valve, with the tapered tip providing a smooth transition through the native valve leaflets so that the prosthetic heart valve is positioned within the aortic annulus. The prosthetic heart valve is expanded (e.g., by expanding a balloon on the delivery catheter) at the aortic annulus.

The method may also include sealing the aorta against the introducer sheath, which may be performed using purse string sutures placed in the aortic tissue around the introducer sheath to cinch around the introducer sheath. This allows a hemostatic seal when the purse strings are tightened around the sheath. The purse strings help with adding tension to the artery walls at it is being brought around the introducer sheath body.

The balloon catheter may incorporate a steering mechanism, and the method may further include steering the balloon catheter within the aortic arch to facilitate positioning the prosthetic heart valve within the aortic annulus.

The balloon catheter may include a tapered segment located just distal to the balloon starts from a tip (which may be narrow but blunted to prevent damage to tissue) and widens to the diameter of the balloon with prosthetic heart valve crimped thereon. The tip may be bent to form a curve which can facilitate advancement of the catheter into the native aortic valve annulus, which may be performed without the need for a guidewire. The curved tip also may serve a protective role, and can allow the catheter to be positioned away from the ventricular walls of the heart.

Note that a guidewire may or may not be used during various portions, or even during the entirety of, the procedures disclosed herein.

A method of the invention may further involve leaving the native aortic valve leaflets in place such that inflating the balloon expands the prosthetic heart valve into contact therewith. Furthermore, a pre-dilation balloon catheter may be inserted prior to the valve delivery balloon catheter, and a balloon thereon inflated to pre-dilate the aortic annulus. Alternatively, the method may include expanding the prosthetic heart valve into contact with a prosthetic heart valve that was previously implanted at the aortic annulus Another off-pump, minimally-invasive surgical method of delivering a prosthetic heart valve to an aortic valve annulus of a patient while the patient's heart remains beating includes providing an expandable prosthetic heart valve in an expanded state and a delivery catheter having a distal end. The heart valve is crimped to a contracted state over the delivery catheter distal end. A relatively small access opening is made in the chest wall to access the aorta. For example, an intercostal access opening (e.g., in the right second intercostal space), also known as a mini-thoracotomy (e.g., right anterior) may be created to access the aorta of the patient, or a ministernotomy may be performed to provide such access, or a subclavian puncture. With access provided to the aorta, an aortic puncture can be formed at or near the aortic arch. An introducer sheath is inserted into the patient's chest via the chest access opening and through the aortic puncture, and the delivery catheter can be advanced through the introducer sheath and into a position in the ascending aorta adjacent the aortic valve annulus. The distal end of the delivery catheter is advanced and steered into the aortic annulus so that the prosthetic heart valve is properly positioned and oriented within the aortic annulus. Finally, the prosthetic heart valve expands at the aortic annulus into contact therewith.

The delivery catheter may include a balloon or other expandable member on its distal end, and the prosthetic heart valve may include a balloon-expandable stent, wherein the step of expanding includes expanding the balloon (e.g., by injecting fluid into the balloon) or other expandable member to expand the prosthetic heart valve outward into contact with the aortic annulus. The delivery catheter may include a restraining sheath or other restraining device on its distal end which holds the prosthetic heart valve in proper position on the delivery catheter. The prosthetic heart valve may include a self-expanding stent, wherein the step of expanding includes releasing the prosthetic heart valve from a restraining device (e.g., restraining sheath) to permit the self-expanding prosthetic heart valve to expand outward into contact with the aortic annulus. For balloon expandable or self-expanding prosthetic heart valve, the native aortic valve leaflets (or leaflets or a previously-implanted prosthetic valve) may be left in place such that the prosthetic heart valve expands into contact therewith. Prior to expanding the expandable prosthetic heart valve, a pre-dilation balloon may be advanced through the puncture and inflated to pre-dilate the aortic annulus.

The present invention further encompasses a minimally-invasive prosthetic heart valve delivery system, including an introducer sheath having a lumen therethrough of no greater than 24 French and a balloon catheter having a balloon on a distal end, the balloon catheter further including a tapered tip for improved advancement into the aortic annulus. In one embodiment, the tapered tip tapers from a maximum width of 4 mm to 10 mm to a minimum width (at the distal tip) of 2 mm or less. In a further embodiment, the distal tip has a diameter of about 1 mm. The tapered tip may have a length of 10 mm to 40 mm between the maximum width and the distal tip, and the tapering may be consistent along the length thereof. The system may include a balloon-expandable prosthetic heart valve crimped over the balloon, wherein the outer dimension of the balloon catheter with the prosthetic heart valve crimped thereon is small enough to pass through the introducer sheath lumen, and the tapered tip provides a generally smooth transition along the delivery catheter from the tip to the crimped prosthetic valve.

The system may be relatively short, such that the balloon catheter has a working length sized to fit into the introducer of no more than about 24 inches (61 cm). At the same time, the introducer sheath may have a total length of no more than about 13 inches (33 cm).

A further understanding of the nature and advantages of the present invention are set forth in the following description and claims, particularly when considered in conjunction with the accompanying drawings in which like parts bear like reference numerals.

BRIEF DESCRIPTION OF DRAWINGS

Features and advantages of the present invention will become appreciated as the same become better understood with reference to the specification, claims, and appended drawings wherein:

DETAILED DESCRIPTION OF THE INVENTION

The heart is a hollow muscular organ of a somewhat conical form. It lies between the lungs in the middle mediastinum and is enclosed in the pericardium. The heart rests obliquely in the chest behind the body of the sternum and adjoining parts of the rib cartilages, and projects farther into the left than into the right half of the thoracic cavity so that about one-third is situated on the right and two-thirds on the left of the median plane. The heart is subdivided by septa into right and left halves, and a constriction subdivides each half of the organ into two cavities, the upper cavity being called the atrium, the lower the ventricle. The heart therefore consists of four chambers; the right and left atria, and right and left ventricles.

Figure 1A:
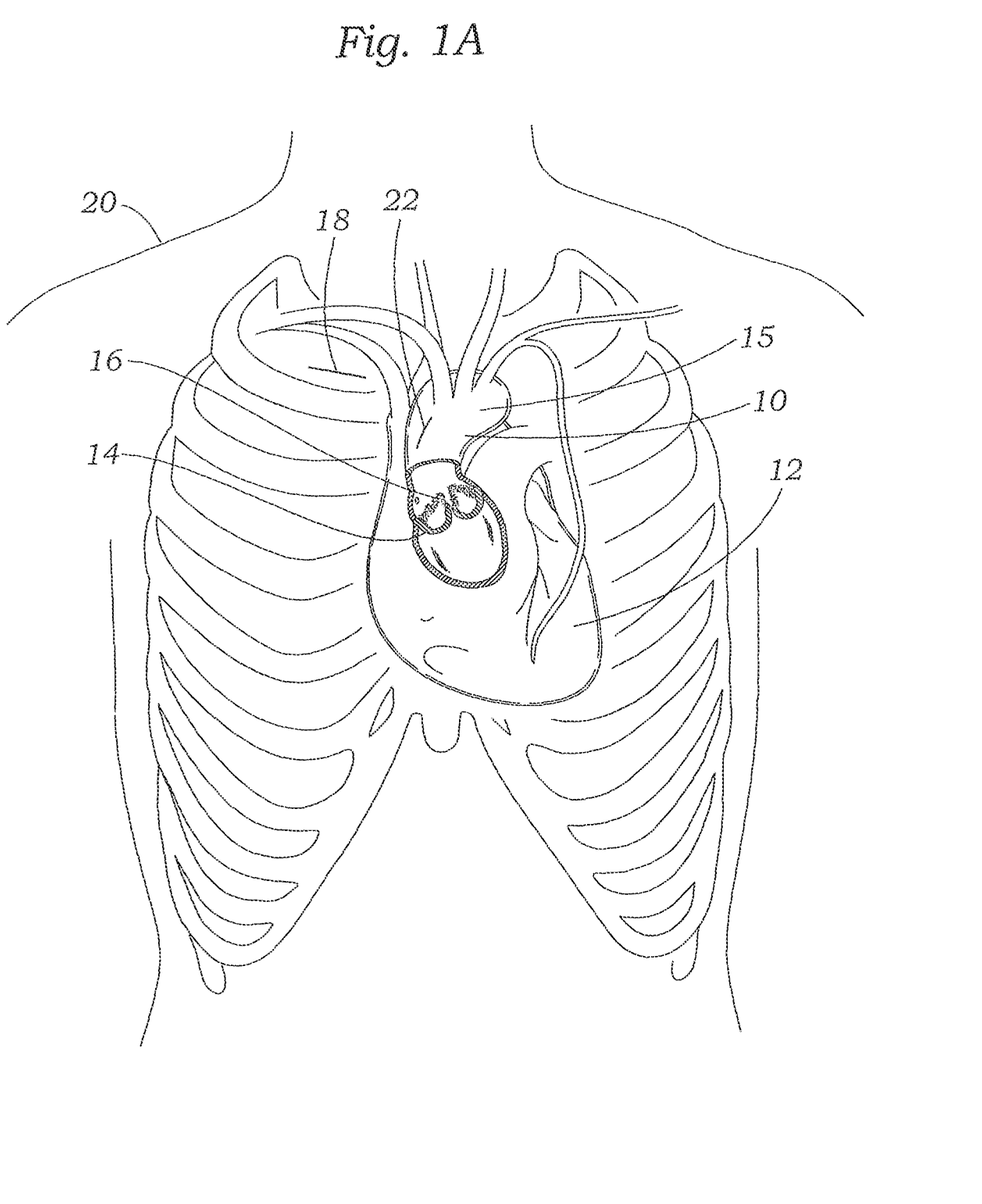
FIG. 1A is a schematic frontal view of a patient showing the location of an intercostal incision and aortic incision providing access into the aortic arch of a patient in accordance with an embodiment of the current invention.
Figure 1B:
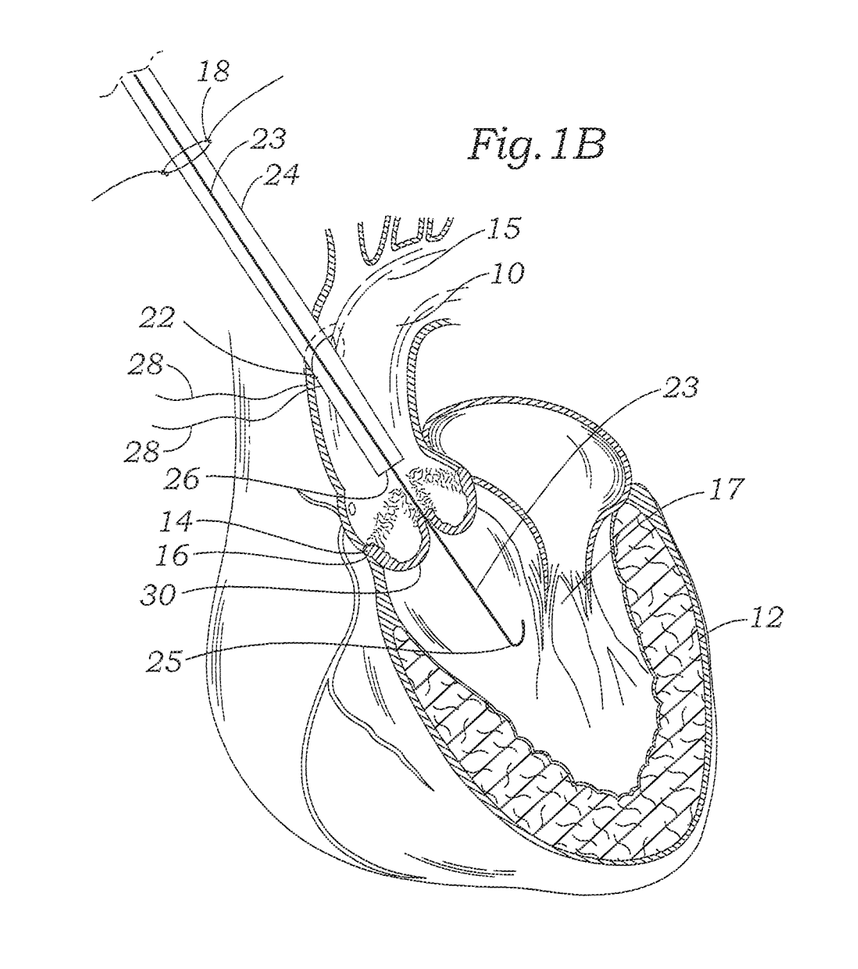
FIG. 1B is a cross-sectional view through the left side of a patient's heart showing a procedure for advancing a guidewire and introducer sheath into the patient in accordance with an embodiment of the current invention.

As seen in FIG. 1A, the aorta 10 extends above the heart 12, starting at the aortic valve 14 and forming the aortic arch 15, which extends above and to the left of the heart (from the perspective of the patient). Access to the aorta 10 and aortic valve 14 may be made via several approaches. For many patients, a direct line-of-sight approach to the aortic valve annulus 16 can be attained, via the aorta 10, starting at a thoracic incision 18 in the patient 20 as shown in dashed line, which in the particular embodiment depicted is positioned at the second right intercostal space. Such an approach is often termed a "mini-thoracotomy." Once access to the aorta 10 is provided (e.g., via intercostal incision), an aortic incision 22 is made in the aorta 10. As depicted in FIG. 1B, a guidewire 23 may be introduced into the aorta 10 via the thoracic incision 18 and aortic incision 22. The guidewire 23 may be advanced so that its distal end 25 crosses the aortic valve 14 and enters the left ventricle 17. Note that the use of the guidewire 23 is optional, depending on the particular application. An introducer sheath 24 may be advanced into the aorta 10 via the thoracic incision 18 and aortic incision 22 (and over the guidewire 23, if present), as depicted in FIG. 1B. The introducer sheath 24 may be flexible or substantially rigid, and may be straight and/or curved. The introducer sheath 24 diameter may be no greater than 24 French, and 22 or 24 Fr may be preferred, or even smaller, such as 18 F or smaller, depending on crimped valve/balloon outer diameter limitations. In one embodiment, the introducer sheath 24 is substantially rigid and substantially straight, and can be advanced in a generally straight line from the thoracic incision 18 thru the aortic incision 22 and adjacent the aortic valve annulus 16. The physician may locate the distal opening 26 of the introducer sheath 24 just to the outflow side of the aortic valve, as seen in FIG. 1B. The position of the introducer sheath 24 relative to the aortic valve 14, as well as the position of other elements of the system, may be monitored using radiopaque markers and fluoroscopy, and/or using other imaging systems such as transesophageal echo, transthoracic echo, intravascular ultrasound imaging (IVUS), and/or an injectable dye that is radiopaque. The guidewire may be advanced into the heart prior to introduction of the introducer sheath, with the sheath being advanced over the guidewire. The order may also be reversed, with the introducer sheath advanced first, and the guidewire introduced through the introducer sheath.

Methods according to the invention may include using an introducer sheath but without the use of a guidewire, using a guidewire without the use of an introducer sheath, using both a guidewire and introducer sheath (as depicted in FIG. 1B), or using neither a guidewire nor introducer sheath.

In one embodiment, sutures 28 are passed through the aortic tissue and around the aortic incision 22, such as in a so-called purse-string configuration, to hold the aortic tissue tightly closed (e.g., against the introducer sheath 24) to prevent blood from leaking out of the aorta. The sutures 28 may be passed through the aortic tissue prior to, during, or after formation of the aortic incision 22, with tension applied to the sutures 28 to hold the aortic incision 22 closed and/or hold the aortic tissue tightly against the introducer sheath 24.

In one embodiment of the present invention, a surgeon implants a prosthetic heart valve over the existing native leaflets, which may be calcified. There are procedures and devices for removing calcified leaflets, but such removal may not be necessary. Therefore, a heart valve replacement procedure that installs the prosthetic heart valve directly over (and thereby containing) the native leaflets may be preferred. However, the calcified native leaflets may present issues in advancing devices through the native valve annulus.

Figure 2A:
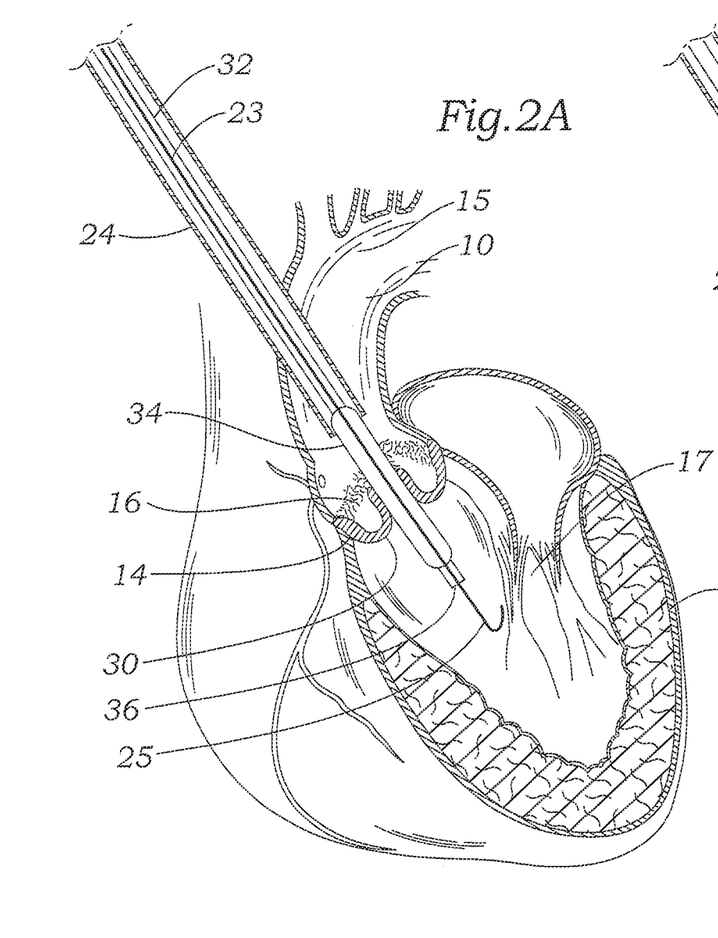
FIGS. 2A-2B are cross-sectional views through the left side of a patient's heart showing a procedure for dilating a calcified aortic annulus prior to implantation of a prosthetic heart valve in accordance with an embodiment of the current invention.
Figure 2B:
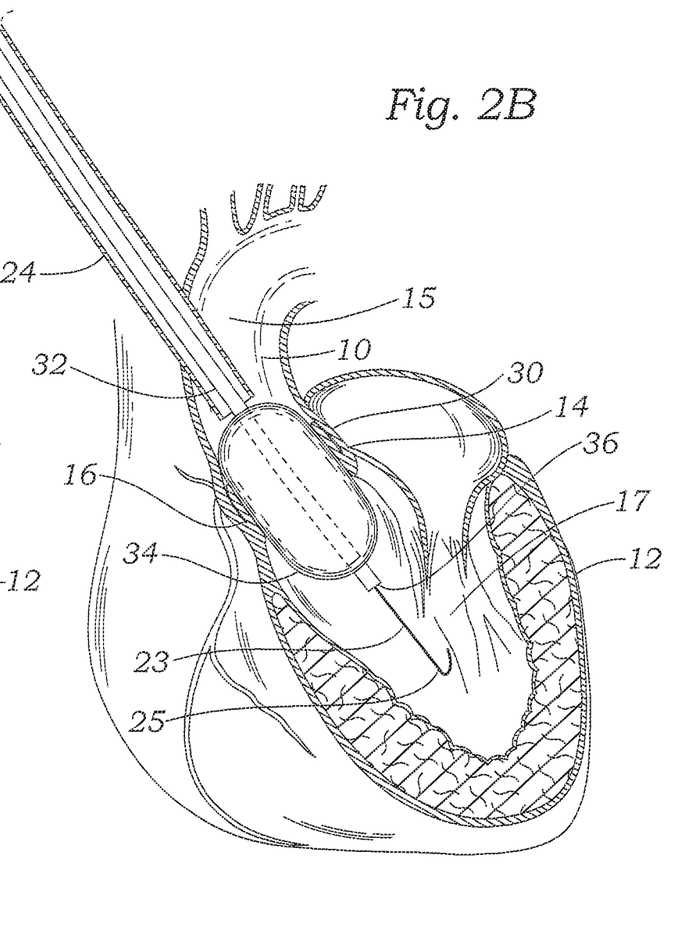

Those skilled in the art will recognize that it may be necessary to pre-dilate the leaflets and annulus of the stenotic aortic valve before deploying a prosthetic valve within the aortic valve. FIGS. 2A and 2B depict a valvuloplasty procedure that may be initially performed to compress the native aortic heart valve leaflets 30 outward against the aortic valve annulus 16 and/or aorta 10. As mentioned above, the native aortic valve leaflets 30 may be substantially calcified, and the valvuloplasty may be necessary to crack and otherwise force apart hardened tissue. Pre-dilatation may increase the flow area through the aortic valve 14 and create an opening in the native leaflets 30 of sufficient size to receive the new prosthetic valve. Pre-dilatation may be achieved using an expandable member, such as a dilatation catheter 32 having a dilatation balloon 34 thereon. One example of pre-dilation of a valve annulus is seen in U.S. Pat. No. 6,908,481 to Cribier, issued Jun. 21, 2005 and expressly incorporated by reference herein.

FIG. 2A illustrates a dilatation catheter 32 with dilatation balloon 34 at a distal end 36 passed through the introducer sheath 24 and into the aorta 10, with the distal tip 36 of the dilatation catheter 32 advanced through the aortic valve 14 and into the left ventricle 17 until the dilatation balloon 34 is positioned within the aortic valve annulus 16. The dilatation catheter distal tip 36 may be tapered and/or curved to facilitate the advancement of the dilatation catheter past the aortic valve leaflets 30 and through the annulus 16. The dilatation balloon catheter tip 36 may be formed in a similar fashion to the delivery catheter tips discussed below and depicted with respect to FIGS. 6-10 (see element 84 therein).

As indicated in FIG. 2B, the dilatation balloon 34 is expanded radially outward into contact with the native aortic valve leaflets 30. The particular dilatation balloon 34 used in a particular procedure and patient may be selected, based on size and other characteristics (e.g., of the native aortic valve), so that it expands outward and nominally compresses the native valve leaflets 30 against the surrounding annulus 16 and/or aortic walls. Assessing the characteristics (size, calcification, etc.) of the particular patient's native aortic valve may be performed using various known methods and devices, including ultrasound. As a result of the valvuloplasty procedure depicted in FIG. 2B, the native valve leaflets are compressed outwardly against the aortic wall and a substantially circular orifice may result. Additional details regarding pre-dilatation and valve replacement can be found in U.S. Patent Publication No. 2003/0014104, filed May 2, 2002, the contents of which are expressly incorporated by reference herein.

The devices and methods disclosed herein are particularly well-suited for replacing a stenotic aortic valve, and as such the native valve dilatation procedure depicted in FIGS. 2A-2B may precede the valve implantation so as to smooth out the contours of the annulus 16 and leaflets 30. It should be noted, however, that the procedure described herein may be performed without valve pre-dilation. Furthermore, the present procedure may be performed as a first time valve implant or to supplement a previous implant. A relatively large proportion of recipients of prosthetic heart valves are older, typically older than 60. Over time, prosthetic heart valves have been known to show reduced performance and even failure. Re-operating on elderly and/or frail patients may be problematic. However, a minimally-invasive procedure such as disclosed herein can eliminate open-heart surgery and potentially cardiopulmonary bypass, and may be desirable for an aging patient. Therefore, the present invention contemplates transaortic implantation of a prosthetic heart valve within an existing prosthetic valve implant. In such a case, a pre-dilation step is typically not necessary, though it is conceivable.

The prosthetic heart valve implantation procedure described herein may be performed in conjunction with cardiopulmonary bypass, or without such bypass in a so-called off-pump procedure. The necessity for bypass depends on a number of factors, including the patient's overall health, age, vulnerability to such a procedure, and condition of the native valve. The implantation procedure may preferably be performed off-pump.

FIGS. 3A-3E depict a method of deploying and implanting a prosthetic heart valve 40 with a delivery catheter 38 with tapered tip 42 in a transaortic approach according to an embodiment of the present invention. The physician may first size the native aortic valve (or previously-implanted prosthetic valve) using, e.g., a physical sizer, echocardiography, and/or other known method (or equivalent thereof). Note that the expandable prosthetic valve 40 may be provided pre-crimped onto the balloon 44 of the delivery catheter 38, or the physician or other operating room personnel may crimp the expandable prosthetic valve 40 over the balloon 44 of the delivery catheter 38. With the expandable prosthetic valve 40 positioned thereon, the physician advances the delivery catheter 38 through the previously-positioned introducer sheath 24.

Figure 3A:
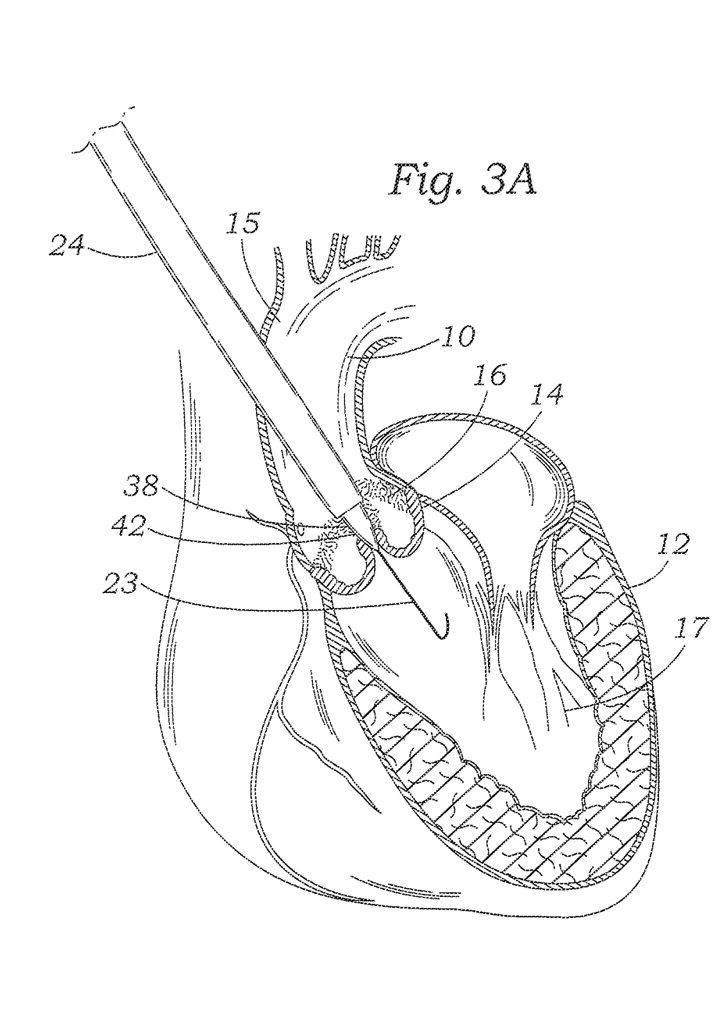
FIGS. 3A-3E are cross-sectional views through the left side of a patient's heart showing several steps in a procedure for implanting a prosthetic heart valve in accordance an embodiment of the current invention.

FIG. 3A shows a delivery catheter introducer sheath 24 positioned in the left ventricle through the aortic incision 22 and over the guidewire 23 that extends downward through the native aortic valve 14. Note that the delivery catheter introducer sheath 24 may be the same introducer sheath depicted in FIGS. 1B-2B for use with the dilatation catheter 32, or may be a (separate) sheath dedicated to use with the delivery catheter.

Figure 3B:
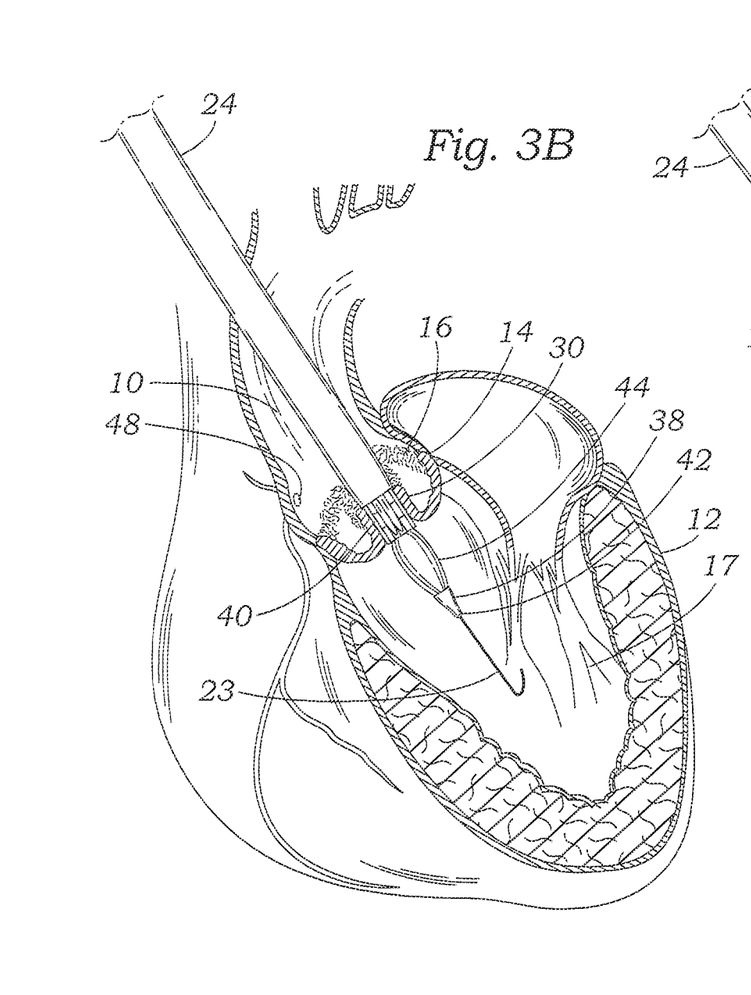
Figure 3C:
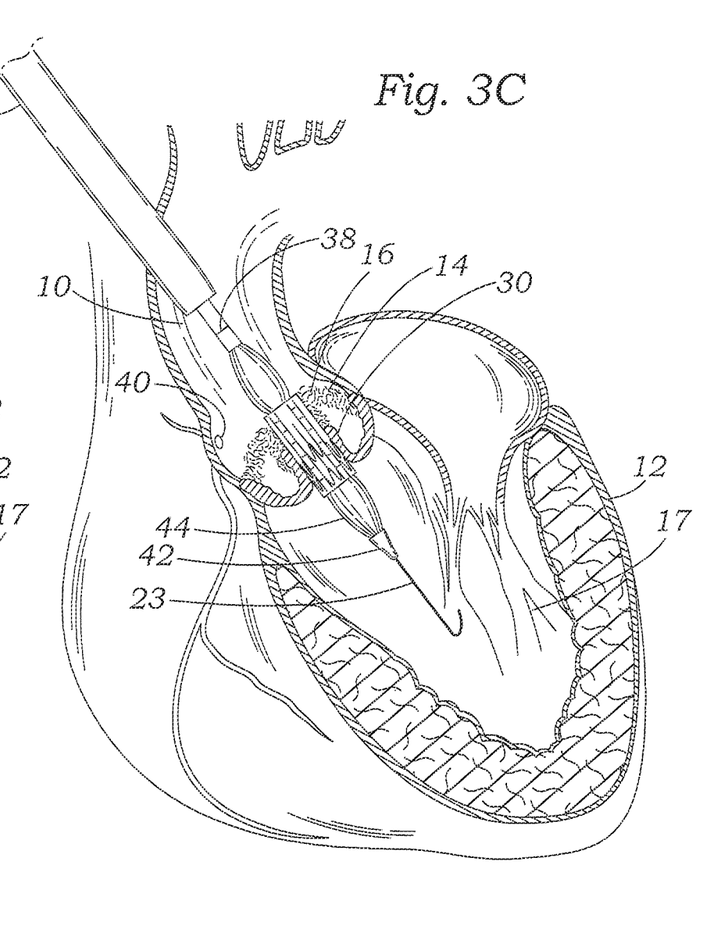

FIG. 3B shows the advancement of the delivery catheter 38 over the guidewire 23 and through the introducer sheath 24 until the prosthetic heart valve 40 is located at the aortic annulus 16 and between the native aortic leaflets 30. FIG. 3C also illustrates retraction of the introducer sheath 24 from its more forward position in FIG. 3B. Radiopaque markers may be provided on the distal end of the introducer sheath 24 and/or valve 40 and/or delivery catheter 38 to more accurately determine their relative positions with respect to each other and to the native structures. During advancement of the delivery catheter 38, a pusher 39 may be positioned just proximal of the crimped prosthetic heart valve 40, which may prevent the prosthetic heart valve 40 from moving proximally with respect to the delivery catheter 38. The pusher 39 is typically retracted to a position proximal of the balloon 44 prior to balloon inflation, as depicted in FIG. 3C.

The precise positioning of the prosthetic heart valve 40 may be accomplished using known methods, such as by locating radiopaque markers on the prosthetic heart valve (e.g., at its distal and proximal ends) and/or on the balloon 44 and/or other part of the delivery catheter 38. The surgeon may adjust the position of the valve 40 by actuating a steering or deflecting mechanism within the delivery catheter 38. Furthermore, the rotational orientation of the prosthetic valve 40 can be adjusted relative to the cusps and commissures of the native valve by twisting the delivery catheter 38 from its proximal end and observing specific markers on the valve 40 or delivery catheter 42 under fluoroscopy. One of the coronary ostia 48 opening into a sinus of the ascending aorta 10 is shown, and those of skill in the art will understand that it may be desirable to avoid occluding the coronary ostia with the prosthetic valve 40. It should also be noted that although the native leaflets 30 of the aortic valve 14 are shown coapting in FIG. 3A, and being flexibly displaced by the delivery catheter 38 in FIGS. 3B and 3C, the native leaflets may actually be in quite different positions, such as being compressed further outward against the aortic annulus from a pre-dilation procedure and/or malformed due to extensive calcification.

Figure 3D:
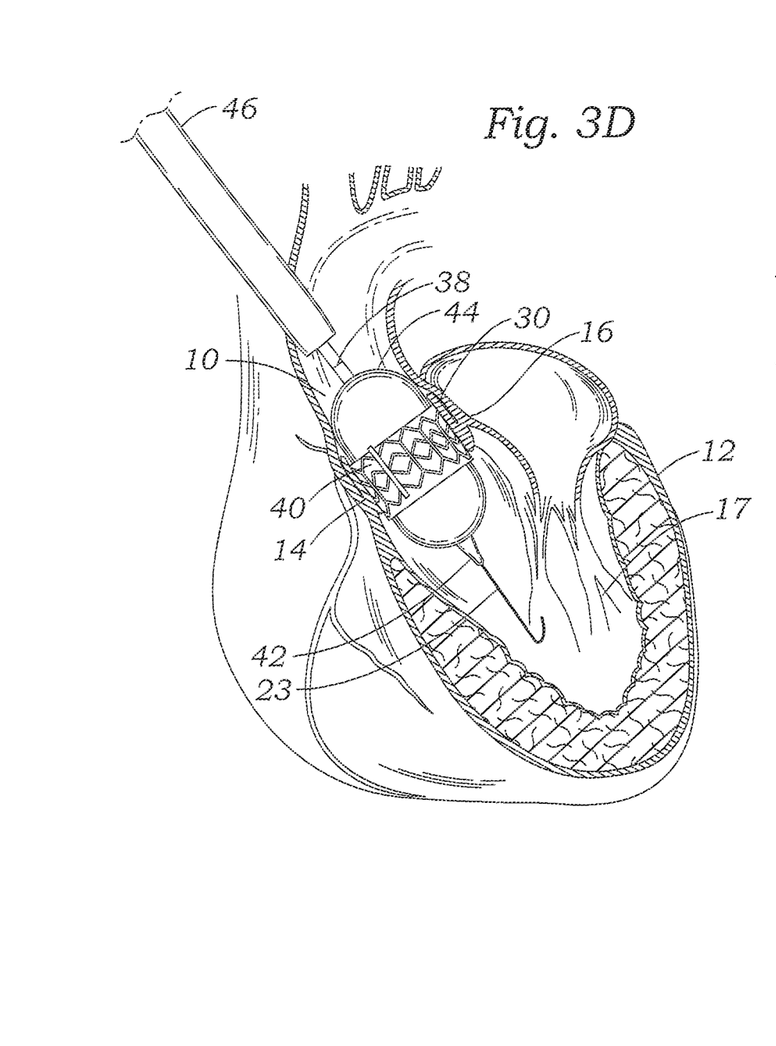

FIG. 3C shows the prosthetic heart valve 40 in its contracted or unexpanded state crimped around the delivery catheter balloon 44. When the physician is satisfied of the proper positioning and rotational orientation of the valve 40, the delivery catheter balloon 44 is expanded as seen in FIG. 3D. Proper size measurement of the native aortic valve 14 and annulus 16 prior to deployment enables the physician to select an optimum-sized valve 40 that will expand outward into good contact with the aortic valve annulus 16. Note that the term "good contact" implies sufficient contact to ensure that the prosthetic heart valve 40 does not migrate after implant.

A number of devices are available to assist in anchoring the prosthetic valve 40 into the aortic annulus, such as barbs and the like. Examples of such anchors for use with a prosthetic heart valve of the present invention are disclosed in co-pending U.S. patent application Ser. No. 10/883,575, filed Jun. 30, 2004, the disclosure of which is expressly incorporated herein by reference. The prosthetic valve 40 can take a variety of different forms but generally comprises an expandable stent portion that supports a valve structure. The stent portion has sufficient radial strength to hold the valve at the treatment site and resist recoil of the stenotic valve leaflets and other adjacent structures. Additional details regarding examples of balloon expandable valve embodiments for use with the invention can be found in U.S. Pat. Nos. 6,730,118 and 6,893,460, the entire contents of both of which are expressly incorporated herein by reference. The prosthetic heart valve 40 may include sufficient irregularity on its outer surface such that it may be anchored in the aortic annulus without the use of barbs or other tissue piercing structures.

Figure 3E:
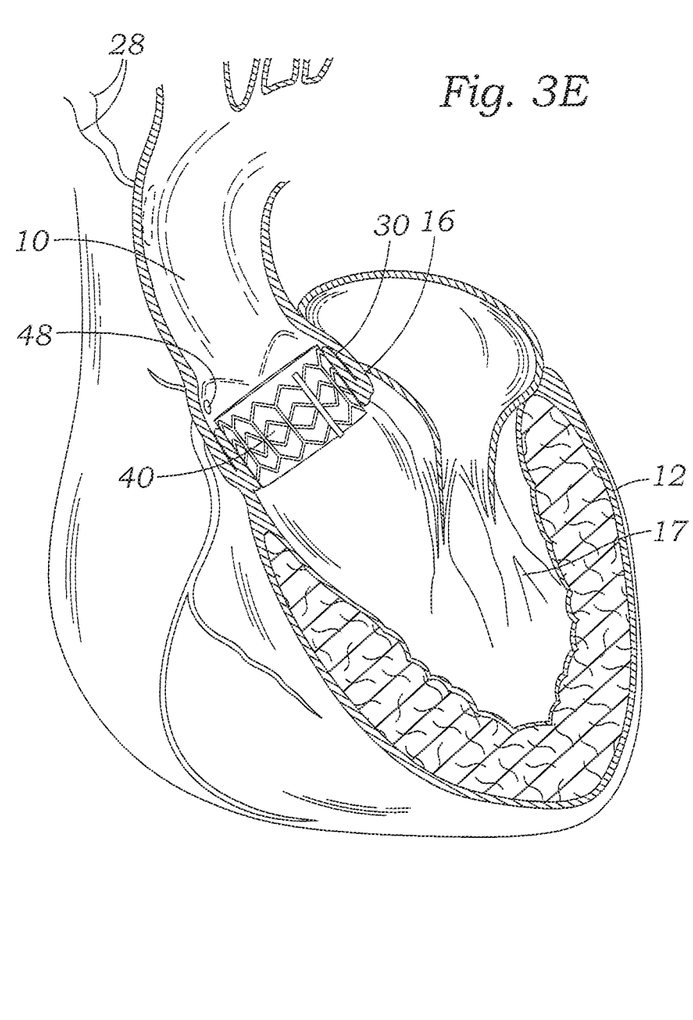

Once the prosthetic valve 40 is properly implanted, as seen in FIG. 3D, the delivery catheter balloon 44 is deflated, and the entire delivery system including the delivery catheter 38 is withdrawn over the guidewire 23. The guidewire 23 is then withdrawn, followed by the introducer sheath 24. Ultimately, the sealing sutures 28 previously described are cinched tight and tied to close the aortic incision 22, as seen in FIG. 3E.

It is important to recognize that the heart valve delivery system of the present invention is particularly well-suited for the retrograde, left ventricular apex, "transaortic," approach. More particularly, the mini-thoracotomy approach requires relatively short instruments. Therefore, the portion of the introducer sheath 24 that extends into the body may desirably be no more than about 8 inches (20 cm) long, and the length of the delivery catheter 38 (and of the dilatation catheter 32) that may extend into the introducer sheath 24, i.e., the "working length," may desirably be no more than about 24 inches (61 cm). Further specifics on general characteristics of delivery catheters and introducer sheaths which may be used with the current invention are presented in co-pending U.S. patent application Ser. No. 11/280,063 filed Nov. 16, 2005, and in co-pending U.S. patent application Ser. No. 11/152,288 filed Jun. 13, 2005, the contents of each of which is expressly incorporated herein by reference. The present system differs in several aspects that make it more suitable for a transaortic approach, although some features are common.

Figure 4:
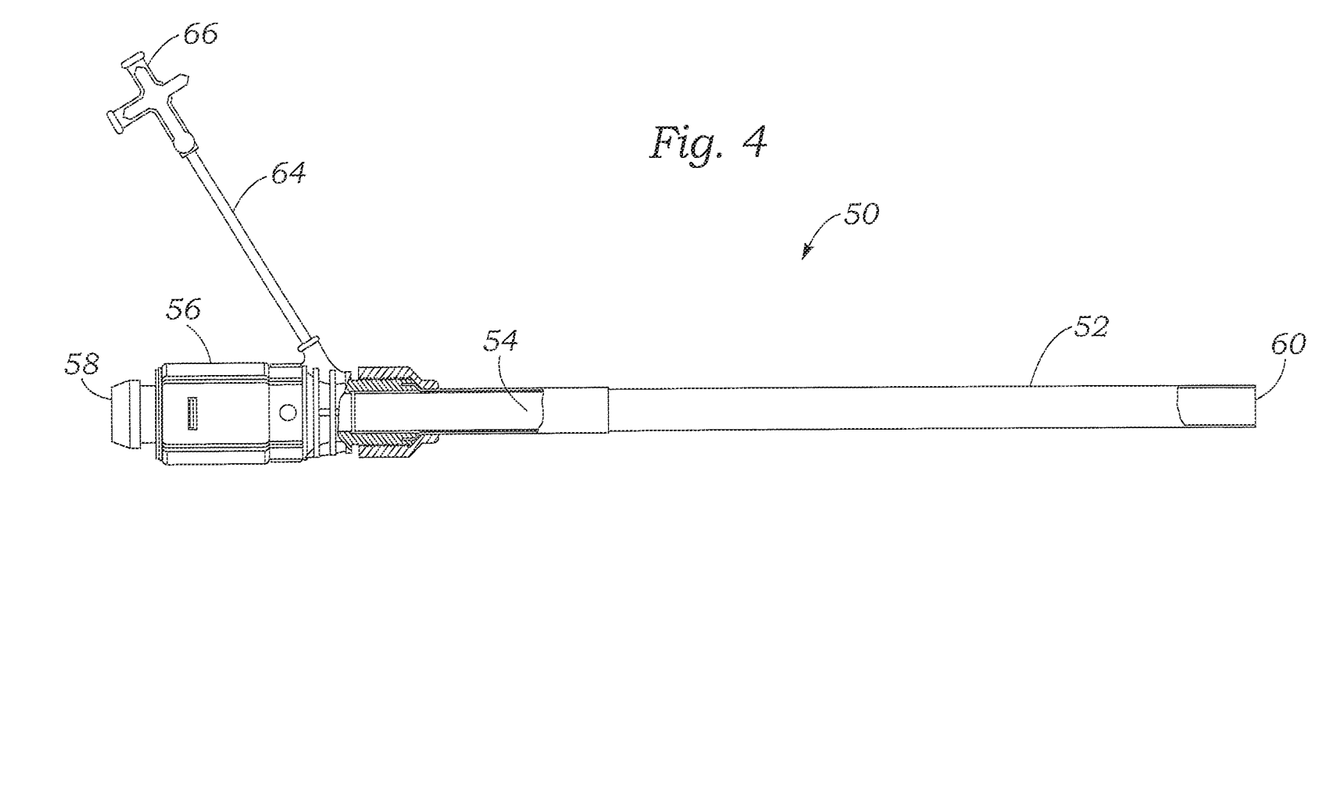
FIG. 4 is a side elevational view of an introducer in accordance with an embodiment of the current invention.

FIG. 4 depicts an example of an introducer 50 having a delivery sheath 52 (which can be used as the sheath 24 depicted in FIGS. 2-3) which forms an internal lumen 54 through which other devices (e.g., balloon catheters, etc.) may be introduced into the patient's heart. The delivery sheath 52 is coupled to an introducer housing 56 containing a series of valves which provide a seal to prevent fluid (e.g., blood) leakage through the internal lumen 54. The valves will prevent leakage when the sheath is free of instruments, and also will provide a tight seal around instruments of various sizes (e.g., diameters) as they are introduced through the introducer. For example, the valves seal around both a guidewire and a balloon catheter, whether introduced together or separately. The delivery sheath 52 can extend into the patient's body and into the heart, with the introducer housing 56 located outside the patient's body. The surgeon or other user can thus remotely introduce instruments into the patient's heart by passing the instruments through the proximal opening 58, into the internal lumen 54, and out of the distal opening 60 of the delivery sheath 52 of the internal lumen and In a preferred embodiment, the introducer sheath 52 possesses an external hydrophilic coating and has a length of about 10 cm to 40 cm, depending on the particular patient and application, so that it may extend through the thoracic incision and aortic incision elements 18 and 22, respectively, in FIG. 1A), into the aorta, and reach the aortic valve annulus.

A side port tube 64 extends away from the introducer and terminates in a three-way stopcock 66. The side port tube 64 enters the lumen 54 at a position distal of the sealing valves in the introducer housing 56. This permits the user to infuse medicaments or other fluids through the lumen 54 of the introducer 50 even if devices such as the balloon catheter are advanced through the proximal opening 58.

Figure 5:
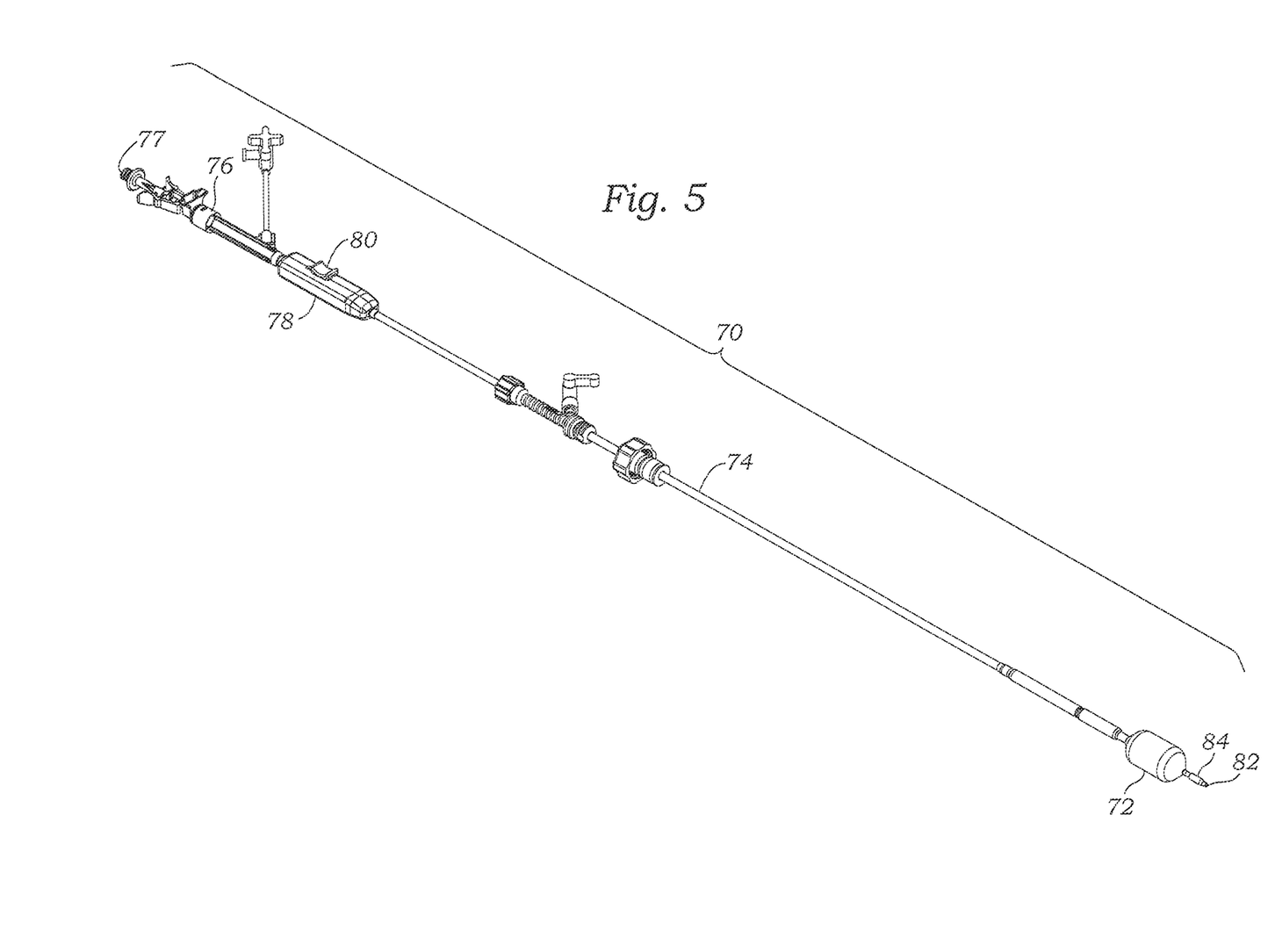
FIG. 5 is a perspective view of a valve delivery catheter in accordance with an embodiment of the current invention.

FIG. 5 depicts an example of a balloon catheter 70 with a balloon 72 thereon, which comprises an assembly of interrelated components along a catheter shaft 74. A proximal portion 76 has a luer fitting 77 and handle 78 with one or more controls 80. A distal end portion has the balloon 72 (on which a prosthetic heart valve can be mounted) and terminates at a distal end 82 in a tapered distal tip 84. Different embodiments of distal portions for such a balloon catheter are also depicted in FIGS. 6 to 10.

The balloon catheter of the present invention may incorporate relatively sliding concentric inner and outer balloon inflation tubes that attach to opposite ends of the balloon. A detailed discussion of the structure and function of this concentric tube configuration may be found in U.S. Pat. No. 5,968,068, the disclosure of which is expressly incorporated by reference herein.

Figure 6:
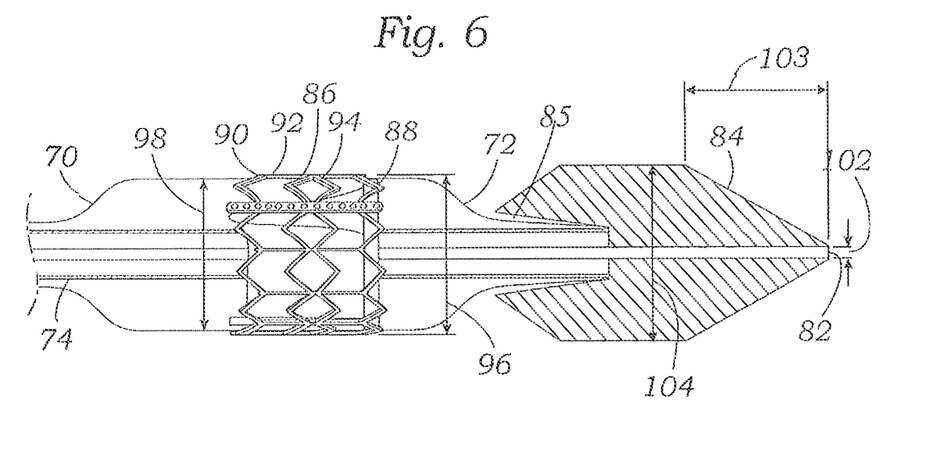
FIG. 6 is a side view, in partial cross-section, of a catheter distal portion in accordance with an embodiment of the current invention.

FIG. 6 depicts a distal portion of a balloon catheter 70 according to an embodiment of the invention. An expandable prosthetic heart valve 86 is positioned on the balloon 72. For a valve being implanted in the aortic annulus via a retrograde approach such as that depicted in FIGS. 1-3, the prosthetic heart valve 86 is positioned with its inlet end 88 positioned distally (with respect to the balloon catheter 70) of its outlet end 90. The prosthetic heart valve 86 comprises a support stent 92 and one-way valve assembly 94 (which may be formed of multiple leaflets). The prosthetic heart valve 86 is crimped or otherwise reduced to a valve delivery diameter 96 (which is typically in the range of 24 F or less) to mate closely with the balloon 72 in a generally deflated state and to reduce the overall system diameter for introduction through the patient's anatomy. The valve delivery diameter 96 is thus close in size to the deflated balloon (maximum) diameter 98 (which is typically in the range of approximately 1.4 mm to 2.5 mm.

A tapered tip 84 is secured at the distal end of the balloon catheter 70. The tapered tip terminates in a distal tip 82, which provides a distal opening for guidewire lumen 100. The tapered tip 84 may start at a very small initial diameter 102 at its distal tip (which may be on the order of 0.04 inches, i.e., similar in size to the guidewire lumen 100). Going proximally along the tapered tip, the diameters increases up to an overall diameter 104 which may be about 24 F or less or so, which may be substantially equal or similar in size to the valve delivery diameter 96. The tapered tip may taper from its widest diameter to its tip along a length 103 of about 10 mm to 40 mm to present an angled surface advantageous for advancement through the anatomy.

The tapered distal tip 84 may be formed of a substantially flexible and soft material, such as polyethylene (which could be low density), PeBax 35D-50D, etc. As the diameter of the tapered distal tip 84 decreases (as it does toward the distal end thereof), the flexibility increases, so that the distal end thereof will give easily if brought into contact with surrounding tissue. The tapered distal tip 84 can thus reduce trauma to surrounding tissue which might come into the catheter tip when the catheter is advanced into the patient.

As depicted in FIG. 6, the balloon 72 may extend distally under the proximal portion of the tapered distal tip 84 with a tight seal formed therebetween, so that the balloon material at the distal portion is sandwiched between the tapered distal tip 84 and balloon catheter shaft 74.

Figure 7:
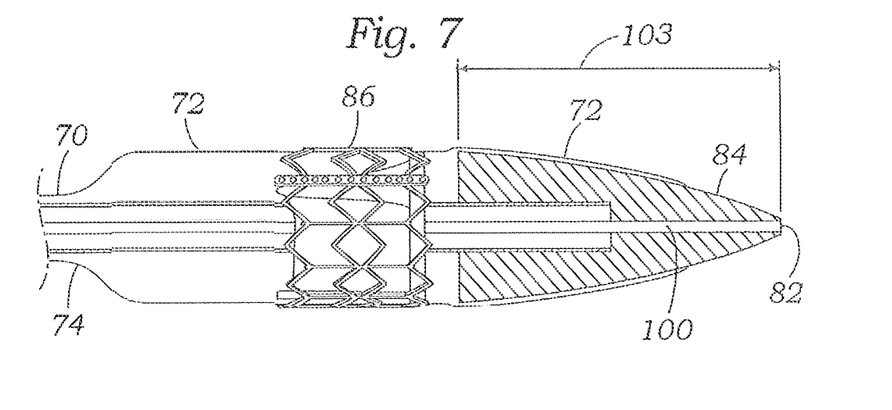
FIG. 7 is a side view, in partial cross-section, of a catheter distal portion in accordance with an embodiment of the current invention.

FIG. 7 depicts a further embodiment, wherein the balloon 72 extends over a tapered distal tip 84 and is tightly secured thereto to form a tight seal. Such an embodiment may provide ease of manufacture and a generally smooth transition from the distal tip to the balloon and to the prosthetic heart valve. The material of the balloon 72 may be secured to the material of the tapered distal tip 84 via various methods, such as adhesive and/or heat treatment.

Figure 8:
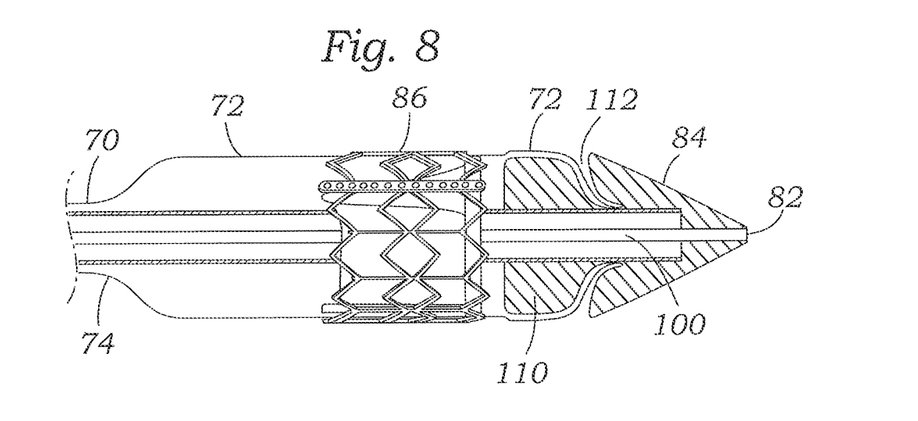
FIG. 8 is a side view, in partial cross-section, of a catheter distal portion in accordance with an embodiment of the current invention.

FIG. 8 depicts a further embodiment of a distal end, wherein a proximal tapered piece 110 over which the balloon 72 passes is provides just proximal of the main body of the tapered distal tip 84, with the balloon 72 at its distal end secured to the tapered tip 84 just distally of the proximal tapered piece 110 to form a tight seal. In the particular embodiment depicted, the balloon 72 is secured within a crevasse 112 formed between the proximal tapered piece and the tapered distal tip 84. The prosthetic valve 86 is secured onto the balloon 72 proximally of the proximal tapered piece 110. The proximal tapered piece 110 may preferably be formed of soft flexible material, such as the same material used for the tapered tip 84. The tapered tip 84 and the proximal tapered piece 110 may be formed of a single piece of the same flexible/soft material. This assembly can provide a substantially continuous profile from the distal tip 82 to the crimped prosthetic valve 86, thereby easing the passage of the prosthetic valve 86 into the native valve annulus.

Figure 9A:
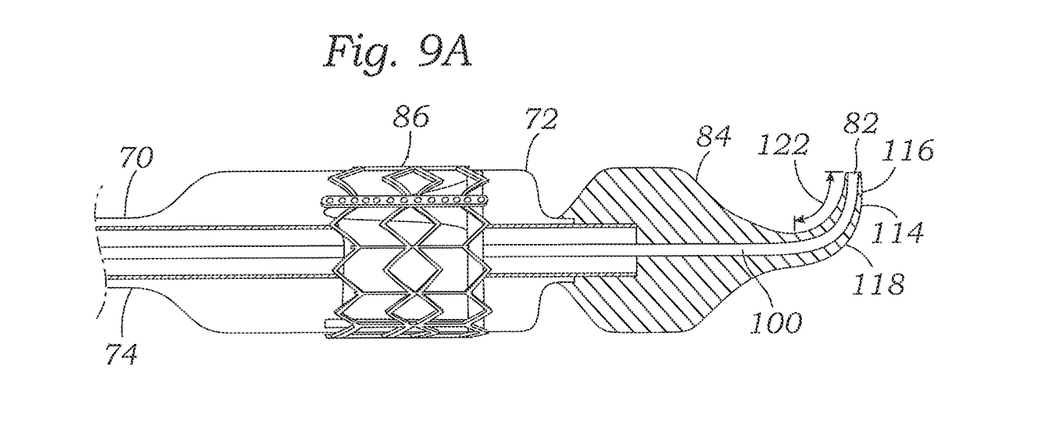
FIGS. 9A-9B are a side views, in partial cross-section, of a catheter distal portion in accordance with an embodiment of the current invention.
Figure 9B:
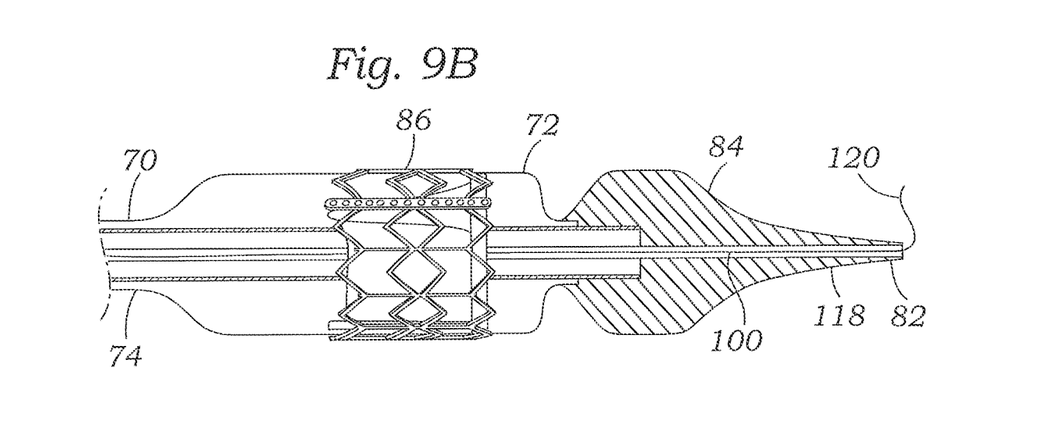

FIGS. 9A-9B depict another embodiment of the invention, wherein a tapered distal tip 84 has a floppy and curled distal section 114. The tapered distal tip 84 is formed from flexible material using known methods so that the distal section 114 is biased toward the curved configuration, as depicted in FIG. 9A. The curved configuration may be exceptionally atraumatic to tissue because the most distal portion 116 when curved will be presented as a "side" of the tapering material, as opposed to the distal tip 82 itself, and also because the curved portion 118 itself serves as a spring-like member to permit the curved tip to curve even more, and thus easily give way, when brought into contact with tissue. The curved portion 118 curves through an angle 122 of approximately 60 to 120 degrees, and in a more specific embodiment about 90 degrees or more, so that the distal tip 82 presents a distal tip surface which faces away from the longitudinal axis of the catheter 70 and/or faces at least partially proximally with respect to the catheter 70, so that if the catheter 70 is advanced distally into tissue the distal tip 82 will contact the tissue sideways via a relatively smooth outer curved side 124 of the tapered section.

As depicted in FIG. 9B, when the distal tip 82 of FIG. 9A is positioned over a guidewire 120, the guidewire 120 itself provides sufficient force to reconfigure the distal tip from the curved configuration into a substantially straight configuration. In the example depicted in FIGS. 9A and 9B, the tapered distal tip 84 tapers from a maximum width to a minimum width (at the distal tip 82) along a length of 10 mm to 60 mm inches.

Figure 10:
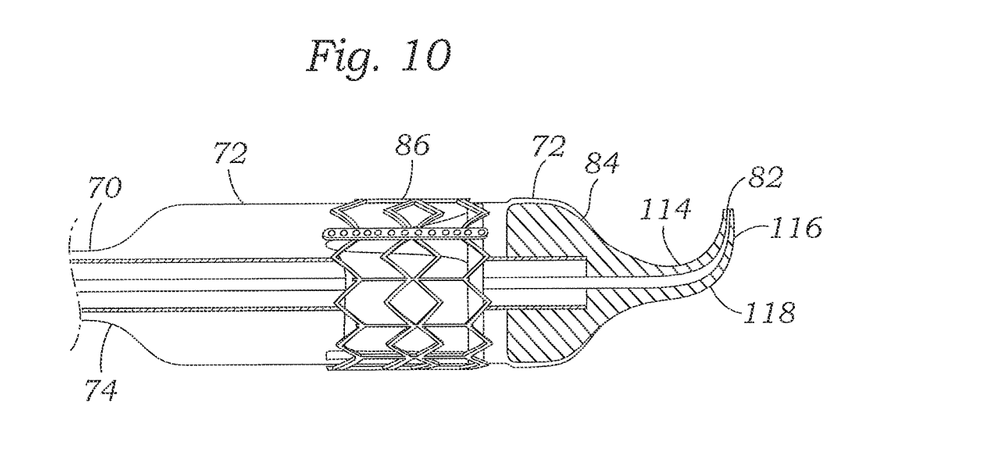
FIG. 10 is a side view, in partial cross-section, of a catheter distal portion in accordance with an embodiment of the current invention.

FIG. 10 depicts a tapered distal tip 84 similar to that of FIG. 9, except the balloon 72 passes around the tapered distal tip and is secured thereto, similar to the fashion depicted previously with respect to FIG. 7.

Figure 11:
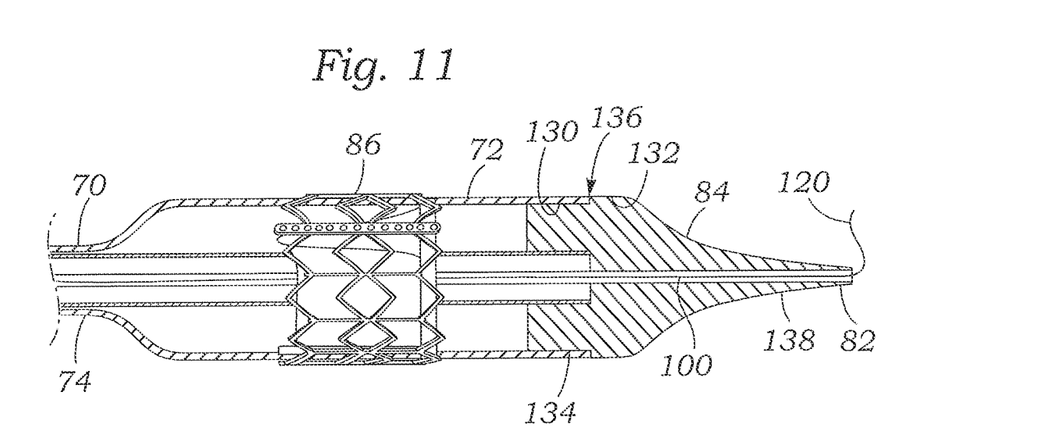
FIG. 11 is side view, in partial cross-section, of another embodiment of a tapered distal tip.

FIG. 11 depicts a proximal depicts a tapered distal tip 84 similar to that of FIGS. 9A-9B and 10, except that the tapered tip portion 84 includes a proximal portion 130 having a slightly smaller outer diameter than the middle portion 132, so that a small recess 134 is created in proximal portion 130 into which a distal portion of the balloon 72 can be placed. The balloon 72 is secured to the proximal portion 130 via methods such as adhesive, heat treatment, etc., to create a tight seal which prevents fluid from leaking out of the balloon 72. The resulting structure creates a relatively smooth outer surface at the transition 136 between the outer surface of the distal tip 84 and the balloon 72. Note that the tapered distal tip 84 may be biased toward a curved configuration (similar to that depicted in FIG. 9A), or the distal section may be biased toward a straightened configuration (such as that depicted in FIG. 9B). A distal tip 84 according to the invention may comprise: as depicted in FIG. 11 (and also in FIGS. 9A. 9B, 10), a concave surface 138 on the forward-facing portion of the distal tip; a convex surface (as depicted in FIG. 7) on the forward-facing portion; or a flat angled surface (as depicted in FIG. 6) on the forward-facing portion. The tapered surfaces (such as the concave surface of FIGS. 9A to 11, etc.) can facilitate advancement of the distal tip through the patient's anatomy, such as when the device is advanced (e.g., in retrograde direction) through a calcified heart valve (such as the aortic valve). For example, a forward-facing concave side surface (such as surface 138 of FIG. 11) can engage against calcified/diseased valve leaflet edges and ease the leaflets aside to permit the catheter to be advanced through a calcified/diseased valve. Distal tips according to the invention may be formed from materials such as molded nylon, and may have maximum diameters of between 0.20 to 0.25 inches which taper to a tip diameter of 0.07 to 0.09 inches. The distal tips may have overall lengths of 0.6 to 0.7 inches, with (in an embodiment such as depicted in FIG. 11) 0.1 to 0.2 inches of that length comprising the proximal portion 130.

The delivery system described herein is particularly well-suited for a retrograde, transaortic approach, partly because of its relatively short length. With reference to FIG. 4, the entire length of the introducer 50 is approximately 13 inches (33 cm), while the length of the sheath 52 that may extend within the body is about 8 inches. The portion of the balloon catheter 70 that extends into the introducer 50 (that is, the portion of the balloon catheter from the distal tapered tip 84 to approximately the handle 78) is no more than about 24 inches (61 cm), which permits about 11 inches (28 cm) of the balloon catheter to extend beyond the introducer distal tip 72. It should be noted that the relatively short length of the delivery system may be unsuited for a longer, more circuitous approach through the peripheral vasculature, such as shown in co-pending U.S. patent application Ser. No. 11/152,288. Also, the steering mechanism, if present, may be provided on the balloon catheter 70 itself, rather than on a secondary catheter used for guiding the balloon catheter, as is done in application Ser. No. 11/152,288. The short length of the balloon catheter and the ability to directly manipulate it greatly enhances successful positioning of the prosthetic heart in the aortic annulus.

While the invention has been described in its preferred embodiments, it is to be understood that the words which have been used are words of description and not of limitation. Therefore, changes may be made within the appended claims without departing from the true scope of the invention. The field of engineering design, which includes the design of structures, systems, devices, and components, is continuously seeking methods for improvement. The process of designing such items is complex and multifaceted, involving the consideration of numerous factors including functionality, efficiency, cost-effectiveness, safety, and regulatory compliance among others.

The invention claimed is:
1. A minimally-invasive prosthetic heart valve delivery system, comprising:
   an introducer sheath with a lumen therethrough;
   a balloon catheter having a distal end with a balloon thereon, the balloon having a prosthetic valve receiving portion, wherein the prosthetic valve receiving portion is configured to have a radially-expandable prosthetic heart valve crimped thereon; and a radially-expandable prosthetic heart valve comprising a support stent and a valve portion, wherein the radially-expandable prosthetic heart valve is configured to be crimped on the prosthetic valve receiving portion of the balloon;

wherein:

the balloon catheter comprises a tapered distal tip positioned on the balloon catheter distally of the prosthetic valve receiving portion, wherein an outer dimension of the balloon catheter having the prosthetic heart valve thereon is small enough to pass through the introducer sheath lumen;

a proximal tapered piece over which the balloon passes is provided proximal of a main body of the tapered distal tip, with the balloon at its distal end secured to the tapered distal tip distally of the proximal tapered piece to form a tight seal;

the balloon is secured within a crevasse formed between the proximal tapered piece and the tapered distal tip; and the prosthetic valve is secured onto the balloon proximally of the proximal tapered piece.

2. The minimally-invasive prosthetic heart valve delivery system of claim 1, wherein the proximal tapered piece is formed of soft flexible material.

3. The minimally-invasive prosthetic heart valve delivery system of claim 1, wherein the proximal tapered piece and the tapered distal tip comprise the same material.

4. The minimally-invasive prosthetic heart valve delivery system of claim 1, wherein the proximal tapered piece and the tapered distal tip comprise different materials.

5. The minimally-invasive prosthetic heart valve delivery system of claim 1, wherein the tapered distal tip and the proximal tapered piece are formed of a single piece of flexible and soft material.

6. The minimally-invasive prosthetic heart valve delivery system of claim 1, wherein there is a substantially continuous profile from the tapered distal tip to the crimped prosthetic valve, thereby easing passage of the prosthetic valve into a native valve annulus.

7. The minimally-invasive prosthetic heart valve delivery system of claim 1, wherein a maximum diameter of the tapered distal tip is substantially equal to a valve delivery diameter of the prosthetic heart valve.

8. The minimally-invasive prosthetic heart valve delivery system of claim 1, wherein the tapered distal tip is approximately conical.

9. A minimally-invasive prosthetic heart valve delivery system, comprising:

an introducer sheath with a lumen therethrough;

a balloon catheter having a distal end with a balloon thereon, the balloon having a prosthetic valve receiving portion, wherein the prosthetic valve receiving portion is configured to have a radially expandable prosthetic heart valve crimped thereon; and a radially-expandable prosthetic heart valve comprising a support stent and a valve portion, wherein the radially-expandable prosthetic heart valve is configured to be crimped on the prosthetic valve receiving portion of the balloon;

wherein:

the balloon catheter comprises a tapered distal tip positioned on the balloon catheter distally of the prosthetic valve receiving portion, wherein an outer dimension of the balloon catheter having the prosthetic heart valve thereon is small enough to pass through the introducer sheath lumen;

a proximal tapered piece over which the balloon passes is provided proximal of a main body of the tapered distal tip, with the balloon at its distal end secured to the tapered tip distally of the proximal tapered piece to form a tight seal;

the balloon is secured within a crevasse formed between the proximal tapered piece and the tapered distal tip;

the prosthetic valve is secured onto the balloon proximally of the proximal tapered piece;

a maximum diameter of the tapered distal tip is substantially equal to a valve delivery diameter of the prosthetic heart valve;

the proximal tapered piece and the tapered distal tip both comprise soft, flexible material; and there is a substantially continuous profile from the tapered distal tip to the crimped prosthetic valve, thereby easing passage of the prosthetic valve into a native valve annulus.

10. The minimally-invasive prosthetic heart valve delivery system of claim 9, wherein the proximal tapered piece and the tapered distal tip comprise the same material.

11. The minimally-invasive prosthetic heart valve delivery system of claim 9, wherein the proximal tapered piece and the tapered distal tip comprise different materials.

12. The minimally-invasive prosthetic heart valve delivery system of claim 9, wherein the tapered distal tip is approximately conical.

13. A minimally-invasive prosthetic heart valve delivery system, comprising:

an introducer sheath with a lumen therethrough;

a balloon catheter having a distal end with a balloon thereon, the balloon having a prosthetic valve receiving portion, wherein the prosthetic valve receiving portion is configured to have a radially expandable prosthetic heart valve crimped thereon; and a radially-expandable prosthetic heart valve comprising a support stent and a valve portion, wherein the radially-expandable prosthetic heart valve is configured to be crimped on the prosthetic valve receiving portion of the balloon;

wherein:

the balloon catheter comprises a tapered distal tip positioned on the balloon catheter distally of the prosthetic valve receiving portion, wherein an outer dimension of the balloon catheter having the prosthetic heart valve thereon is small enough to pass through the introducer sheath lumen;

a proximal tapered piece over which the balloon passes is provided proximal of a main body of the tapered distal tip, with the balloon at its distal end secured to the tapered distal tip distally of the proximal tapered piece to form a tight seal;

the balloon is secured within a crevasse formed between the proximal tapered piece and the tapered distal tip;

the prosthetic valve is secured onto the balloon proximally of the proximal tapered piece;

a maximum diameter of the tapered distal tip is substantially equal to a valve delivery diameter of the prosthetic heart valve;

the tapered distal tip and the proximal tapered piece are formed of a single piece of flexible and soft material; and there is a substantially continuous profile from the tapered distal tip to the crimped prosthetic valve, thereby easing passage of the prosthetic valve into a native valve annulus.

14. The minimally-invasive prosthetic heart valve delivery system of claim 13, wherein the tapered distal tip is approximately conical.

15. The minimally-invasive prosthetic heart valve delivery system of claim 13, wherein the tapered distal tip and the proximal tapered piece each have a maximum diameter, and the maximum diameters are substantially the same.

* * * * *